US00PP19590P2

(12) United States Plant Patent
Gutter

(10) Patent No.: US PP19,590 P2
(45) Date of Patent: Dec. 23, 2008

(54) ***PENSTEMON* PLANT NAMED 'PENHARWI'**

(50) Latin Name: *Penstemon hartwegii*
Varietal Denomination: Penharwi

(75) Inventor: Martien Everett Gutter, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/977,706

(22) Filed: Oct. 25, 2007

(51) Int. Cl.
*A01H 5/00* (2006.01)

(52) U.S. Cl. ..... Plt./465

(58) Field of Classification Search ..... Plt./465
See application file for complete search history.

*Primary Examiner*—Annette H Para
(74) *Attorney, Agent, or Firm*—S. Matthew Edwards

(57) ABSTRACT

A new *Penstemon* plant particularly distinguished by its pinkish-white flower color, early flowering, and good branching habit.

1 Drawing Sheet

Latin name of the genus and species of the plant claimed: *Penstemon hartwegii.*
Varietal denomination: 'Penharwi'.

BACKGROUND OF THE NEW PLANT

The present invention comprises a new distinct cultivar of *Penstemon,* botanically known as *Penstemon hartwegii.*

The new *Penstemon* is a product of a planned breeding program conducted in Enkhuizen, Netherlands. The new *Penstemon* cultivar has a well branched plant habit, a white to light pink flower color, and is early flowering.

The new *Penstemon* is propagated by cuttings resulting from a single seedling. This seedling originates from a selection in *Penstemon hartwegii* 'Gigant' (not patented), identified as number 'G4915.' An inbred was made of this selection through one cycle of half sib selection (several selections are planted together and are pollinated with the total cloud of pollen of all of these plants, but are harvested per female plant). This was done in the period of June 2003 until November 2003 in Enkhuizen, Netherlands. The seeds of this half sib selection were sown in January 2004 and the seedling was selected in July 2004 in Enkhuizen.

The present cultivar has been repeatedly asexually reproduced by cuttings in Enkhuizen, Netherlands, since 2004. The distinctive characteristics of this new *Penstemon* are stable and reproduced true to type in successive generations of asexual reproduction.

The new *Penstemon* plant is a perennial in zones 4 to 9 in the US.

DESCRIPTION OF THE DRAWING

The new *Penstemon* plant is illustrated by the accompanying photographic drawing which shows blooms, buds and foliage of the plant in full color, the color showing being as true as can be reasonably obtained by conventional photographic procedures.

BOTANICAL DESCRIPTION OF THE PLANT

The following detailed descriptions set forth the distinctive characteristics of this new *Penstemon.* The data which defines these characteristics were collected from asexual reproductions carried out in Enkhuizen, Netherlands. The plant history was taken on 15 week old plants. The instant plant was grown in an 11 cm container in an outdoor container field.

Color references are primarily to the R.H.S. Colour Chart of The Royal Horticultural Society of London.

Plants of the new *Penstemon* differ primarily from the plants of the originator 'Gigant' in the following characteristics:

Plants of the new *Penstemon* start flowering earlier and are more branched than plants of the originator 'Gigant.'

TABLE 1

DIFFERENCES BETWEEN THE NEW CULTIVAR 'PENHARWI' AND A SIMILAR CULTIVAR

| | 'Penharwi' | 'White Bedder' (Not patented) |
|---|---|---|
| Attitude of flower cluster | Upright | Drooping |
| Flower color | Pinkish white | True white |
| Branching | Very good | Medium |

The plant: Classification—Botanical: *Penstemon hartwegii.*
Parentage:
*Originator selection.*—'Gigant' (Not patented).
Propagation:
*Type of cutting.*—Terminal cuttings.
*Time to initiate roots.*—12–16 days at 18° C.
*Time to produce a rooted cutting.*—3 weeks.
*Root description.*—Fine, fibrous and white in color.
Plant description:
*Form.*—Compact basal rosette.
*Size.*—65 cm tall and 28 cm wide.
*Habit.*—Suffrutescent, foliage does not die down in winter.
The foliage:
*Type.*—Simple.
*Arrangement.*—Opposite.
*Shape.*—Lanceolate.
*Venation.*—Pinnate.
*Margins.*—Entire, undulate.
*Apex.*—A cuminate.

*Base.*—Sessile, obtuse.
*Length.*—9.1 cm.
*Width.*—2.9 cm.
*Vestiture.*—Glabrous.
*Texture.*—Leathery.
*Leaf color.*—Upper surface: 137A. Lower surface: 143B.

The inflorescence:
*Type.*—Thryse, virgate and weakly second.
*Number of flowers.*—*8–35* per cyme.
*Peduncle.*—Height: 48 cm. Diameter: 3 cm. Color: 144B. Texture: Glabrous.
*Pedicel.*—Length: 1–1.5 cm. Diameter: 1–2 mm. Texture: Glabrous. Color: 146C.
*Flowering period.*—From June until August.
*Flower bud.*—Length: 3.7 cm. Width: 3.8 cm. Position: Closed tubular, bulging. Color: 46C.
*Flower type.*—Zygomorphic.
*Flower shape.*—Tubular, bilabiate.
*Flower tube.*—Length: 0.5 cm. Width: 0.2 cm.
*Number of flower lobes.*—Five; 2 upper lobes, three lower lobes.
*Flower size.*—Length: 2.6 cm. Width: 2.4 cm.
*Flower color.*—45C; center N155A .
*Calyx.*—Number of lobes : 5, overlapping. Length: 0.7 cm. Width: 0.5 cm. Color: 144A.
*Calyx lobes.*—Apex: Acuminate. Margin: Entire.
*Lastingness.*—On the plant: Each cyme blooms for about 3 weeks on the plant. In the vase: 4 days.

Reproductive organs:
*Stamen.*—Number: 5. Shape: Dehiscent.
*Anther color.*—158A.
*Pollen color.*—158D.
*Pistil length.*—2.7 cm.
*Pistil color.*—64B.
*Fragrance.*—None.
*Filament length.*—2.5 cm.
*Filament color.*—155B.

Seed development: Seed development has not been observed to date.

Disease tolerance: No disease/pest resistance has been observed to date.

Weather resistance: The new *Penstemon* plant is resistant to temperatures ranging from −6° C. till +42° C.

What is claimed is:

1. A new and distinct variety of *Penstemon* plant named 'Penharwi,' as substantially illustrated and described herein.

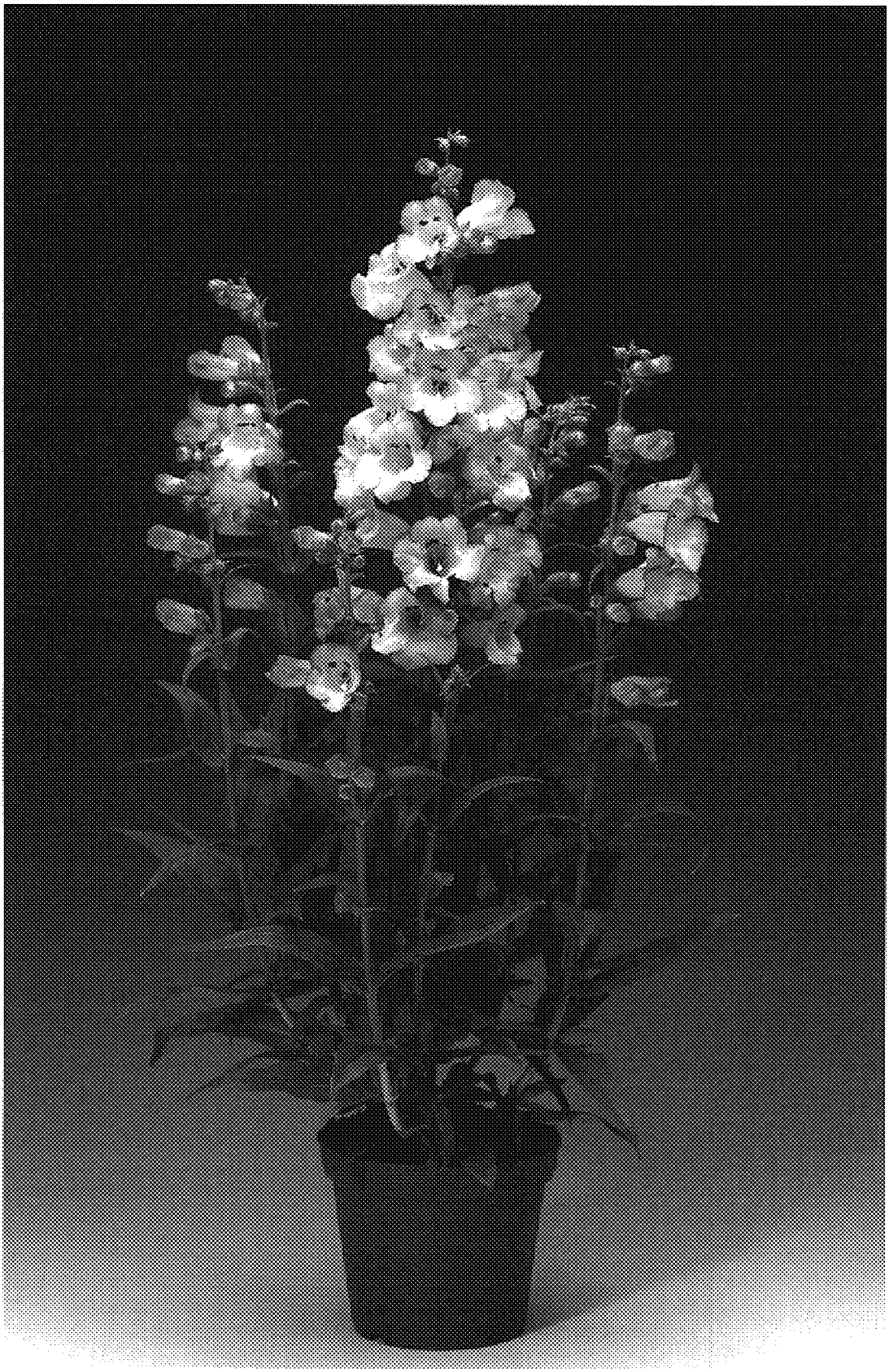

* * * * *